(12) United States Patent
Chang (10) Patent No.: US 7,338,634 B2
(45) Date of Patent: Mar. 4, 2008

(54) QUANTITATIVE FECAL EXAMINATION APPARATUS

(76) Inventor: Mao-Kuei Chang, 1st Floor, No. 24, Lane 78, Hsin-Ai Road, Nei-Hu District, Taipei (114) (TW) 114

( * ) Notice: Subject to any disclaimer, the term of this patent is extended or adjusted under 35 U.S.C. 154(b) by 847 days.

(21) Appl. No.: 10/789,046

(22) Filed: Feb. 25, 2004

(65) Prior Publication Data

US 2004/0179976 A1    Sep. 16, 2004

(30) Foreign Application Priority Data

Mar. 14, 2003  (TW) .............................. 92203938 U (51) Int. Cl.
*G01N 21/00* (2006.01)
(52) U.S. Cl. ............................ 422/56; 422/58; 422/61; 422/101; 436/66; 436/169; 436/904
(58) Field of Classification Search ................. 422/102
See application file for complete search history.

(56) References Cited

U.S. PATENT DOCUMENTS

| 4,563,332 | A | * | 1/1986 | Mitchell et al. | ............ 422/100 |
| 4,849,173 | A | * | 7/1989 | Chang | .......................... 422/56 |
| 5,066,463 | A | * | 11/1991 | Chang | .......................... 422/56 |
| 6,030,582 | A | * | 2/2000 | Levy | ............................ 422/99 |

\* cited by examiner

*Primary Examiner*—Walter D. Griffin
*Assistant Examiner*—Bobby Ramdhanie (57) ABSTRACT

A quantitative fecal examination apparatus includes a fecal collector removably mounted on a container base, having the fecal collector provided with a suction portion for sucking a fecal specimen into the collector and then the fecal specimen is disposed into the container base for examination test or for sucking the fecal specimen for further laboratory test including microscopic inspection, and having a quantitative design in the examination apparatus for collecting the fecal sample in a pre-set quantity for more precise examination.

4 Claims, 8 Drawing Sheets

QUANTITATIVE FECAL EXAMINATION APPARATUS

BACKGROUND OF THE INVENTION

This application is an improvement over the U.S. Pat. No. 5,066,463 entitled "Multiple-purpose Fecal Examination Apparatus" (hereinafter called as "prior art") also issued to the same inventor of this application.

The prior art however has the following drawbacks:
1. For pick-up or releasing of fecal sample, the rake member (120) formed on the handle means 1 may be used. However, there is no suction mechanism for sucking the fecal sample. It will be difficult to collect liquid or loose stool specimen.
2. No quantitative device is provided for picking up the fecal sample quantitatively.
3. The examination procedure is complex, inconvenient and may easily cause contamination to the surrounding, especially when conducting an occult blood test in the upper hollow portion (20) and extension tube (23).

The present inventor has found the drawbacks of the prior art and invented the present quantitative fecal examination apparatus.

SUMMARY OF THE INVENTION

The object of the present invention is to provide a quantitative fecal examination apparatus including a fecal collector removably mounted on a container base,having the fecal collector provided with a suction portion for sucking a fecal specimen into the collector and then the fecal specimen is disposed into the container base for examination test or for sucking the fecal specimen for further laboratory test including microscopic inspection,and having a quantitative design in the examination apparatus for collecting the fecal sample in a pre-set quantity for more precise examination.

The present invention provides a convenient compact and hygienic examination unit for examining fecal specimen or sample.

DETAILED DESCRIPTION

As shown in FIGS. 1~10,a quantitative fecal examination apparatus of the present invention comprises: a collector means 1 removably mounted on a container base 2.

Figure 5:
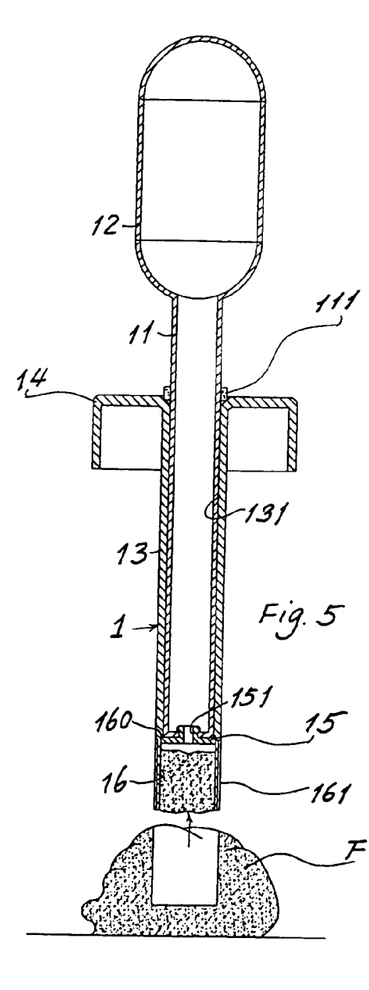
FIG. 5 is a sectional drawing of the collector means for picking the specimen.
Figure 6:
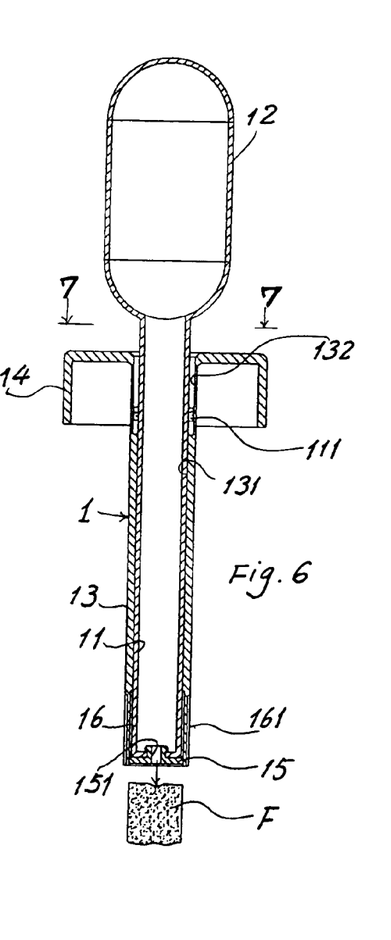
FIG. 6 is a sectional drawing of the collector means when releasing the specimen.

The collector means 1 includes: a hollow stem 11 having a suction (or pumping) portion 12 formed on a top of the stem 11,a sleeve member 13 removably secured in the container base 2 and slidably engaging with the hollow stem 11 having a cap 14 formed on top of the sleeve member 13 for covering the container base 2,a plunger 15 formed on a bottom of the hollow stem 11 and slidably moving in a quantitative chamber 16 formed in a lower portion 161 of the sleeve member 13 (FIG. 5 to FIG. 6).

The plunger 15 and the bottom of the stem 11 arte respectively formed with an aperture 151,110 for air inlet or outlet from the stem 11 when operating the suction portion 12.

Figure 7:
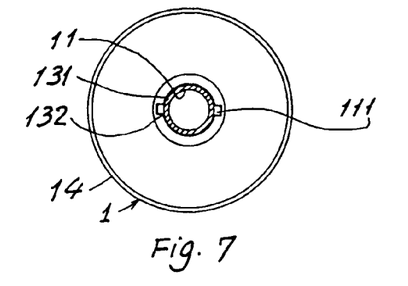
FIG. 7 is a cross sectional drawing when viewed from Line 7-7 of FIG. 6.

The sleeve member 13 includes a pair of slots 132 longitudinally recessed in a central hole 131 formed through the sleeve member 13 for slidably engaging a pair of positioning keys 111 diametrically formed on the hollow stem 11 (FIGS. 6 and 7).

The lower portion 161 of the sleeve member 13 is formed with corrugations on an outside surface on the lower portion 161 for adhering the fecal specimen thereon for easy visual inspection.

Figure 3:
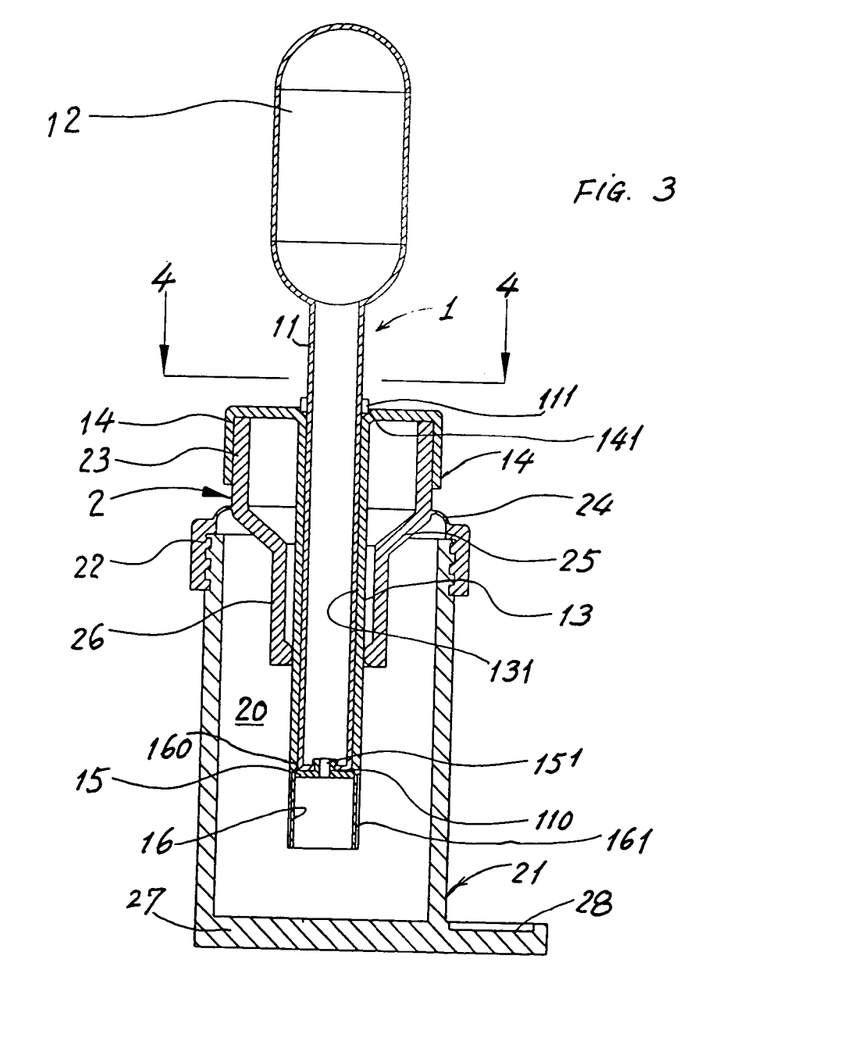
FIG. 3 is a sectional drawing of the present invention when assembled.
Figure 4:
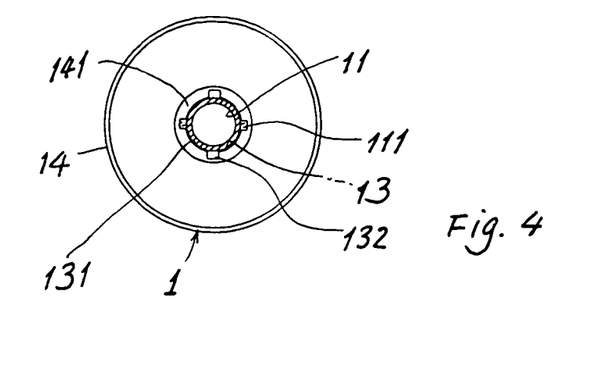
FIG. 4 is a cross sectional drawing of the present invention when viewed from Line 4-4 of FIG. 3.

As shown in FIG. 3,the pair of positioning keys 111 on the hollow stem 11 are rested or held on an annular seat portion 141 concentrically formed on the cap 14 around the central hole 131 in the sleeve member 13,whereby the plunger 15 is kept at an "upper dead point" 160 (a stopping portion 160 in the sleeve member 13) of the quantitative chamber 16 (FIGS. 3,5) in order to collect a quantitative fecal speciment F into the chamber 16; and upon a downward movement of the stem 11 to allow the plunger 15 to thrust the fecal specimen F downwardly (FIG. 6),for example,to be discharged into the container base 2 for examination.

Since the plunger 15 is reciprocated within the quantitative chamber 16 in the sleeve member 13,the fecal specimen as collected into the chamber 16 or released from the chamber 16 will have a volume equal to the internal volume of the chamber 16,thereby collecting or disposing the fecal specimen in a quantitative amount.

Figure 8:
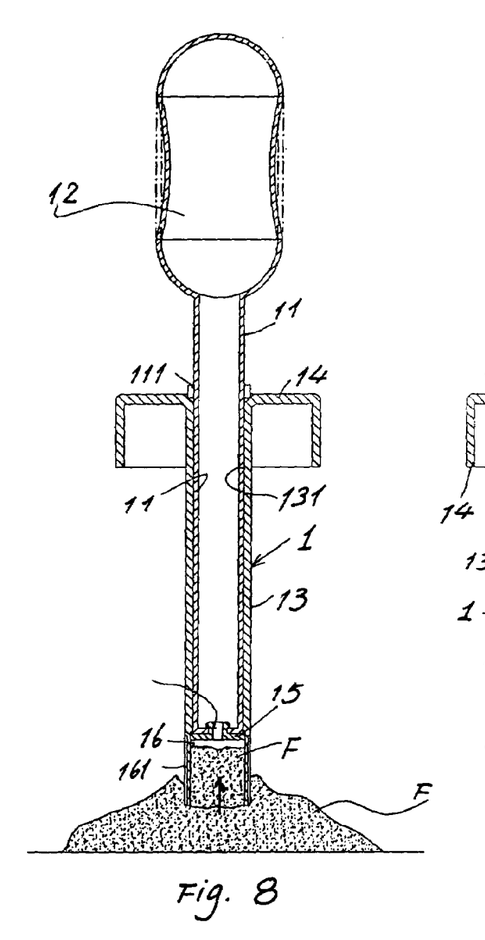
FIG. 8 is a sectional drawing of the collector means for sucking specimen therein.
Figure 9:
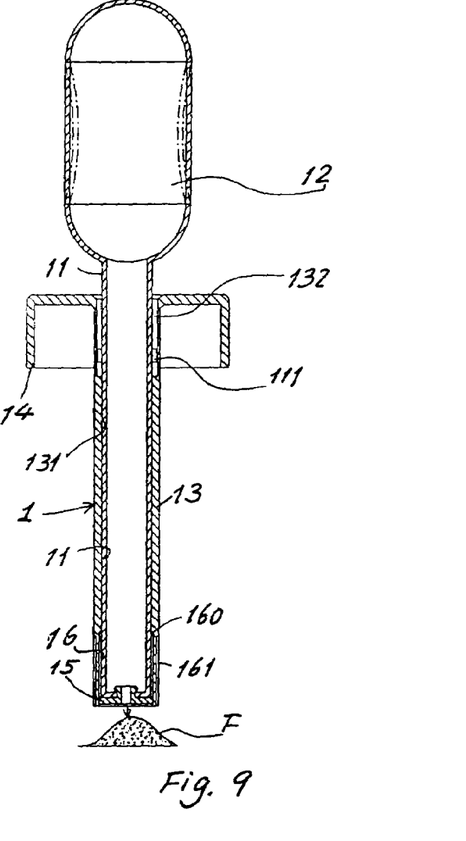
FIG. 9 shows the releasing of specimen from FIG. 8.

The suction portion 12 may be formed with a bulb or a pumping device fixed on the top of the hollow stem 11 for sucking (or releasing) the fecal specimen especially a liquid or loose fecal specimen as shown in FIGS. 8,9. The aperture 151 provides an air inlet or outlet passage during the suction or pumping action when operating (depressing or releasing) the suction portion 12.

A downward movement of the plunger 15 will be limited when the keys 111 on the stem 11 are downwardly retained by the bottom end portions of the slots 132 as shown in FIG. 6.

The container base 2 includes: a container portion 21 which may be formed as a transparent bottle defining an interior 20 in the container portion 21 for filling the fecal specimen F and test reagent therein,and a cover 22 detachably secured on an upper portion of the container portion 21 having a holding cylindrical portion 23 protruding upwardly from the cover 22 to be engaged with the cap 14 of the collector means 1 for removably mounting the collector means 1 on the container base 2 (FIG. 3).

The holding cylindrical portion 23 is downwardly connected with a tapered conical portion 25 which is in turn connected with a lower tube portion 26 to be disposed around the sleeve member 13 when inserting the sleeve member 13 and the hollow stem 11 into the container base 2 (FIG. 3).

Figure 10:
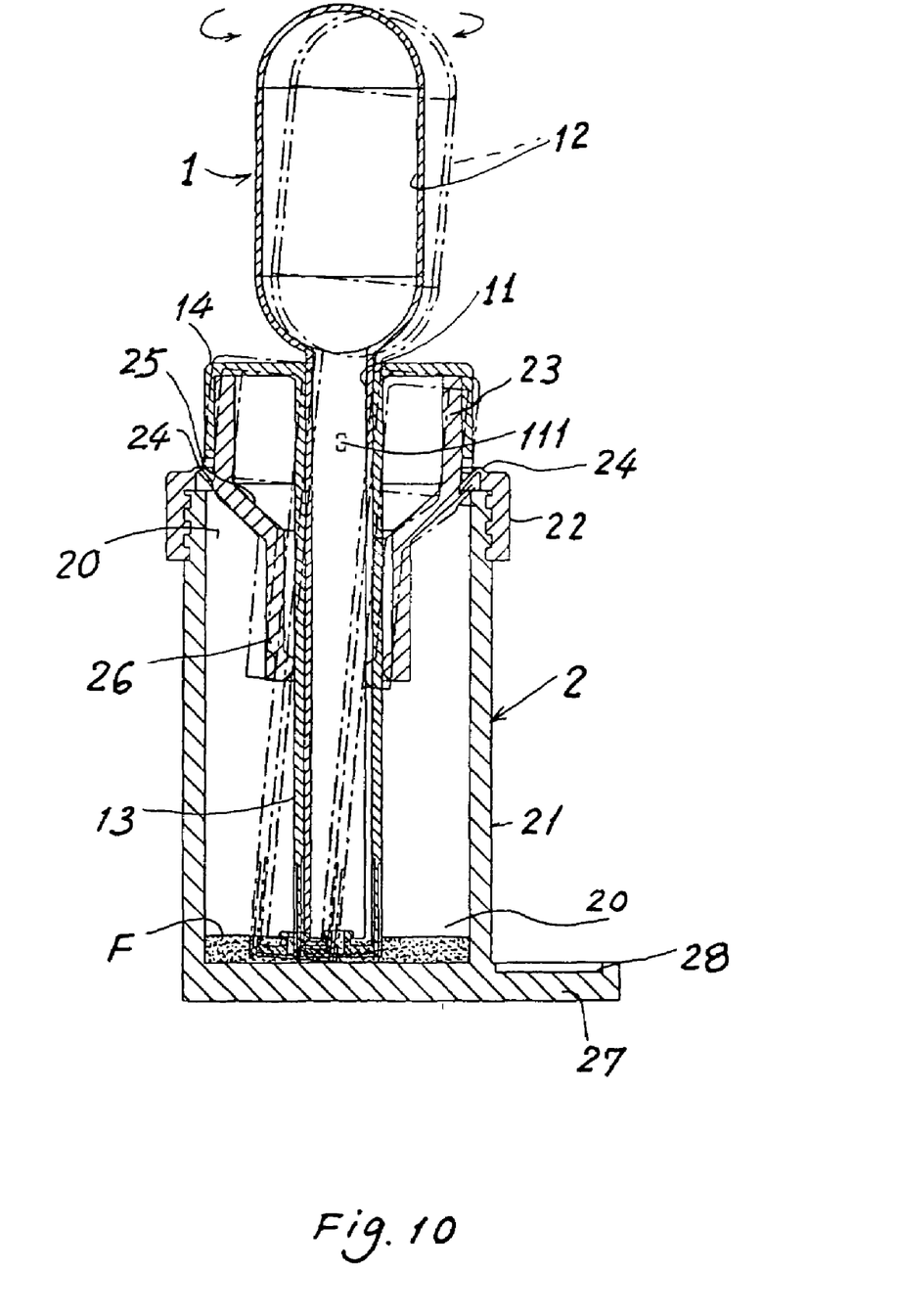
FIG. 10 is an illustration showing the agitation of the specimen when added with a test reagent therein.

The holding cylindrical portion 23 is connected with the cover 22 with a flexible shoulder portion 24, allowing a universal movement such as the agitation of the collector means 1 within the container base 2 for mixing the fecal specimen F with a test reagent as shown in FIG. 10. The flexible shoulder portion 24 may be made as thin as possible such as made of rubber or plastic materials to provide its flexibility. The tapered conical portion 25 also serves to scrap any excess fecal sample when inserting the sleeve member 13 into the lower tube portion 26 in the container base 2.

The container base 2 includes a base portion 27 formed on a bottom of the container base 2 to be stably held on a laboratory table surface.

A quality-control testing platform 28 is formed on the base portion 27 for checking the quality of test reagent such as provided for occult blood test as used in this invention.

The testing platform 28 includes a first test pool 281 wherein a positive test reagent or a high-sensitivity reagent (such as O-toluidine or tetra-methyl benzidine and hydrogen peroxide for occult blood test) may be added into the first test pool 281 (FIG. 1); and a second test pool 282 wherein a negative test reagent or a low-sensitivity reagent (such as Guaiac resin or Lignumvitae resin and hydrogen peroxide for occult-blood test) is dripped into the second test pool 282 for respectively checking the quality and reliability of the two reagents.

Figure 1:
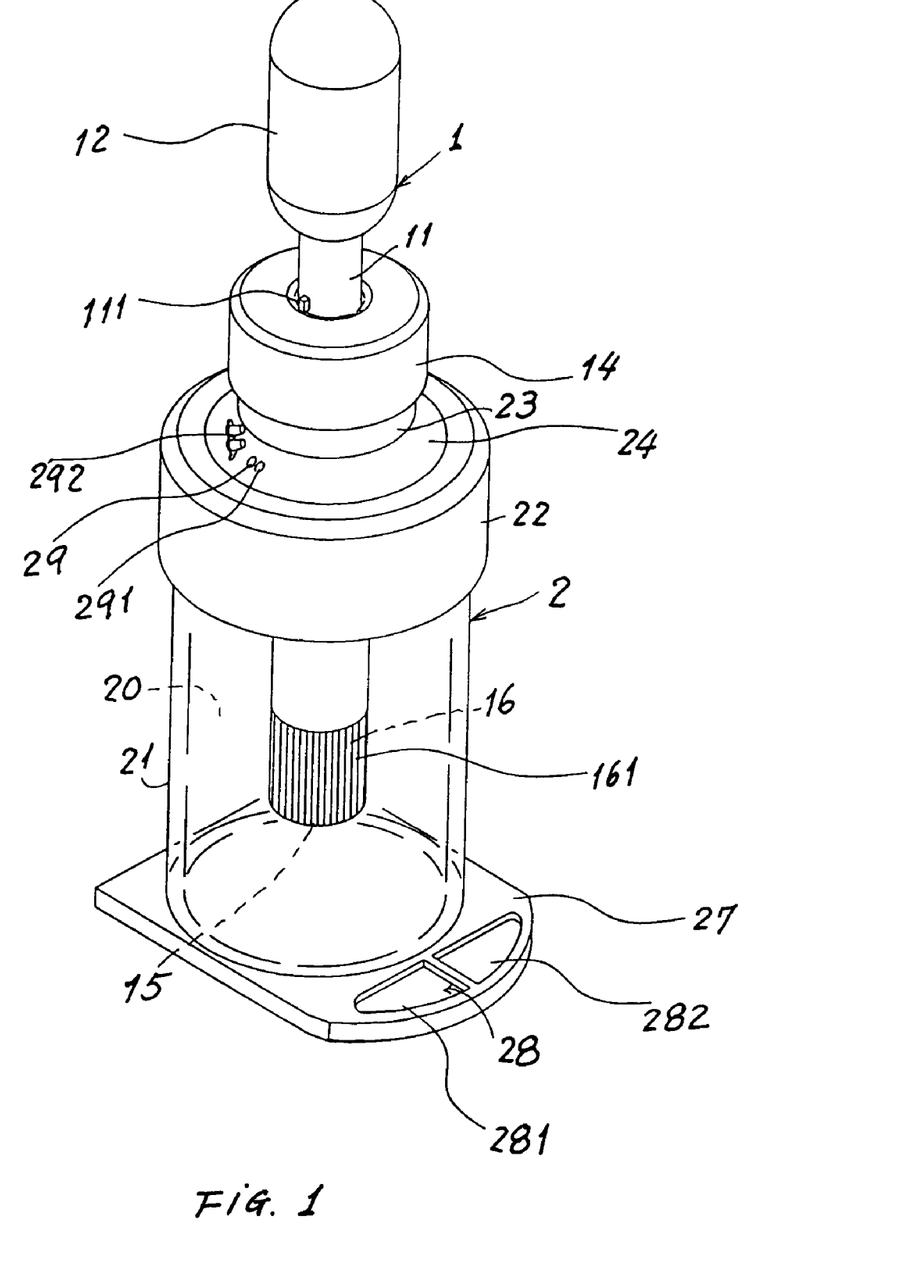
FIG. 1 is a perspective view of the present invention.
Figure 2:
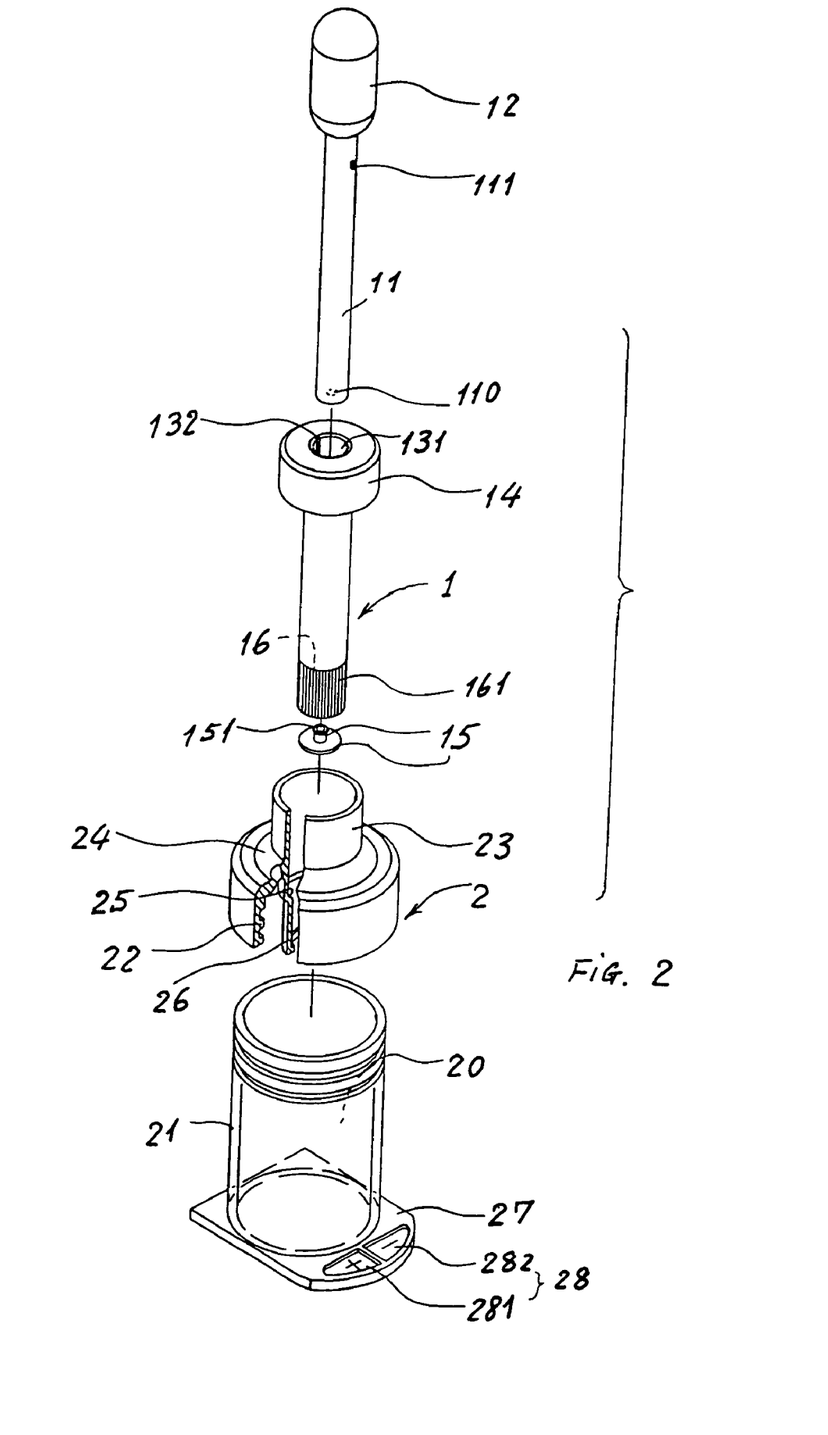
FIG. 2 is an exploded view showing the elements of the present invention.

As shown in FIG. 1, a filling port 29 is formed in the container base 2 such as in the flexible shoulder portion 24 for filling the test reagent into the container portion 21 when a fecal specimen has been collected and stirred therein such as shown in FIG. 10; and a vent 291 is formed in the container base 2 for venting air outwardly to ensure a smooth filling of specimen and reagent into the container portion 21.

During the transport of the examination apparatus of the present invention, a plug 292 as formed on the container base 2 may be provided for closing the filling port 29 and vent 291 for hygienic reason.

After a patient's fecal specimen F has been put into the container portion 21, a test reagent such as the above-mentioned occult blood test reagent is added by a pipette or syringe into the container portion 21. If it reveals a blue color change, it indicates a positive occult blood with hemorrhage present in the fecal sample.

Accordingly, the present invention provides a compact examination unit for a hygienic, smooth and convenient fecal examination to be superior to the prior art. The fecal sample (even liquid one) can be easily collected a disposed by the suction portion 12 of the collector means 1. The quantitative chamber 16 formed in the collector means 1 also provides a quantitative sampling of fecal sample for improving the examination reliability and precision to be superior to the prior art.

Figure 11:
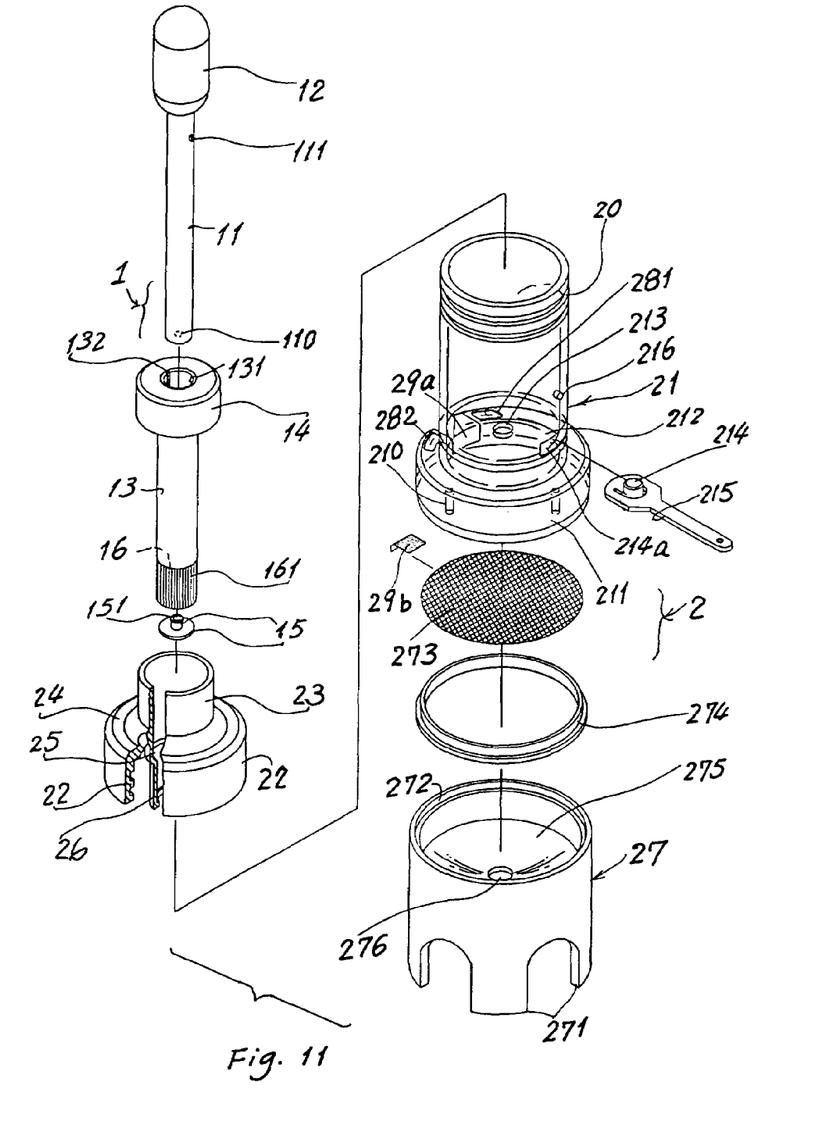
FIG. 11 shows another preferred embodiment of the present invention with exploded elements.
Figure 12:
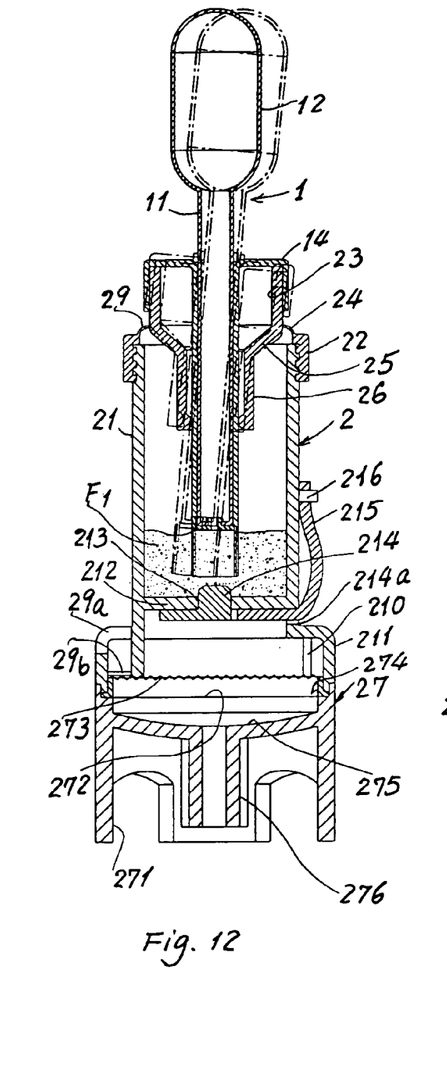
FIG. 12 is a sectional drawing of the present invention when assembled from FIG. 11 and filled therein with reagent and specimen.
Figure 13:
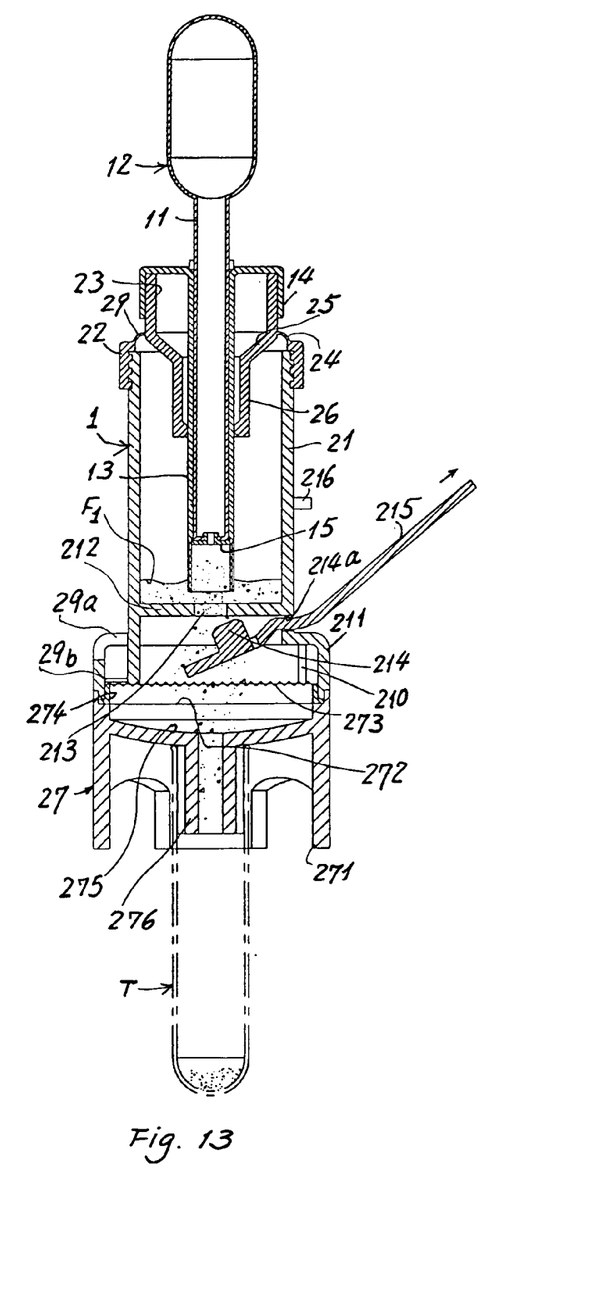
FIG. 13 shows the present invention adapted for centrifugal examination following FIG. 12.

Another preferred embodiment of the present invention is shown in FIGS. 11~13, in which the collector means 1 is the same as the aforementioned; while the container base 2 is modified to have the base 27 to be adapted for connection to a centrifugal test tube T.

The container base 2 includes: a container portion 21 preferably made as transparent bottle, a cover 22 detachably secured to an upper portion of the container portion 21 for removably mounting the collector means 1 in the container portion 21, a base portion 27 secured to a bottom portion of the container portion 21, having a hopper portion 275 formed in a lower portion of the base portion 27 for receiving a fecal solution $F_1$ (which is formed by mixing a fecal sample and a reagent) as drained from the container portion 21 and having a drain tube 276 protruding downwardly from the hopper portion 275 to be connected to a centrifugal test tube T for centrifugal examination (FIG. 13).

A filter 273 is formed in between the container portion 21 and the hopper portion 275 of the base portion 27 for filtering any unexpected suspension matters or dirts in the fecal solution $F_1$.

The base portion 27 includes an upper rim 272 engaged with a lower periphery 211 of the container portion 21 as sealed by a packing ring or a retainer ring 274, having a plurality of retaining rods 210 formed in a bottom portion of the container portion 21 to retain the filter 274 between the retaining rods 210 and the retainer ring 274 retained between the lower periphery 211 of the container portion 21 and upper rim 272 of the base portion 27.

The base portion 27 further includes a plurality of supporting legs 271 to be supported on a frame or holder (not shown).

The container portion 21 further includes: a valve 214 movably secured in the lower periphery 211 of the container portion 21 for normally sealing a drain opening 213 formed in a bottom plate 212 of the container portion 21 provided for stirring a fecal solution $F_1$ in the container portion 21 (FIG. 12).

The valve 214 includes a lever 215 protruding outwardly through a notch 214a cut in the lower periphery 211 of the container portion 21, having a clip or pin 216 formed on the container portion 21 for normally receiving the lever 215 of the valve 214, whereby upon a withdrawal or operation of the lever 215 of the valve 214 to open the opening 213, the fecal solution $F_1$ may be drained into the base portion 27 to be received by the test tube T connected to the base portion 27 (FIG. 13) for further centrifugal examination.

The container portion 21 includes a filling port 29 for filling test reagent or saline solution into the container portion through the filling port, and a test port 29a formed in the lower periphery 211 for dripping occult blood test reagent onto the filter 273, and a test paper 29b which is laid on the filter 273 and positioned below the test port 29a, whereby upon dripping of the test reagent onto the test paper 29b on the filter 273, the color change (for instance from red to blue) on the test paper will indicate the test result of occult blood test. Since the fecal solution may be dispersed due to capillary effect, the fecal solution will be osmosed to the test paper 29b through the filter 273, the reagent as dripped onto the test paper will thus be reacted on the test paper to show the test result.

A quality-control testing platform 28 as aforementioned may also be provided on the container portion 21 such as on the lower periphery 211 as shown in FIG. 11, including a first test pool 281 and a second test pool 282, respectively formed on a rim portion of the lower periphery 211 for checking the effectiveness of the test reagents on the respective pools 281, 282.

The advantages of the present invention has been described as aforementioned. Conclusively, it provides a compact examination unit for a smooth easily-operating fecal examination apparatus, which can be provided for quantitatively collecting and disposing fecal sample by suction or pumping operation.

The present invention may be modified without departing from the spirit and scope of the present invention.

Although the present invention is entitled "quantitative fecal examination apparatus", it may also be essentially defined as a "semi-quantitative" examination unit or the like, not limited in this invention.

The cover 22 is removably secured on the container portion 21 by means of male and female threads. However, other joining methods may also be applied in this invention.

I claim:

1. A fecal examination apparatus comprising:
   a collector means including: a hollow stem having a suction portion formed on said stem, a sleeve member removably secured in the container base and slidably engaging the hollow stem and having a cap formed on a top of said sleeve member for capping the container base; said hollow stem having a pair of positioning keys diametrically formed on said stem and slidably engaging a pair of slots longitudinally recessed in a central hole formed through said sleeve member, said sleeve member having a quantitative chamber formed in a bottom or lower portion of said sleeve member for reciprocatively engaging a plunger formed on a bottom of said hollow stem in said quantitative chamber in said sleeve member; and said sleeve member including a stopping portion formed in said sleeve member for limiting an upward movement of said plunger in said quantitative chamber, and each said slot having a bottom slot end portion for limiting each said positioning key of said hollow stem when downwardly moved; and
   a container base formed as a bottle for filling a fecal sample or specimen and reagent therein;
   whereby upon operation of said suction portion, a fecal sample including liquid or loose stool will be sucked inwardly into said collector means and will be collected or filled into said container base for examination.

2. A fecal examination apparatus according to claim 1, wherein said container base includes: a container portion formed as a transparent bottle defining an interior in the container portion for filling the fecal specimen and test reagent therein, and a cover detachably secured on an upper portion of the container portion having a holding cylindrical portion protruding upwardly from the cover to be engaged with a cap on the sleeve member for removably mounting the collector means including the hollow stem and the sleeve member on the container base; and said holding cylindrical portion downwardly connected with a tapered conical portion which is downwardly connected with a lower tube portion to be disposed around the sleeve member when inserting the sleeve member and the hollow stem into the container base.

3. A fecal examination apparatus according to claim 1, wherein said container base includes: a container portion, a cover detachably secured to an upper portion of the container portion for removably mounting the collector means in the container portion, a base portion secured to a bottom portion of the container portion, having a hopper portion formed in a lower portion of the base portion for receiving a fecal solution which is formed by mixing a fecal sample and a reagent as drained from the container portion and having a drain tube protruding downwardly from the hopper portion to be connected to a centrifugal test tube for centrifugal examination; said container base including a filter formed in between the container portion and the hopper portion of the base portion for filtering suspension matter or dirt in the fecal solution; and said container portion including a plurality of retaining rods formed in a bottom portion of the container portion to retain said filter between the retaining rods and a retainer ring retained between a lower periphery of the container portion and an upper rim of the base portion.

4. A fecal examination apparatus according to claim 3 wherein said container portion includes a filling port for filling test reagent into the container portion through the filling port, and a test port formed in a lower periphery of the container portion for dripping occult blood test reagent onto the filter, and a test paper which is laid on the filter and positioned below the test port.

* * * * *